US010822630B2

(12) United States Patent
Leiske et al.

(10) Patent No.: US 10,822,630 B2
(45) Date of Patent: *Nov. 3, 2020

(54) PROCESS FOR MANIPULATING THE LEVEL OF GLYCAN CONTENT OF A GLYCOPROTEIN

(71) Applicant: AMGEN INC., Thousand Oaks, CA (US)

(72) Inventors: Daniel R. Leiske, Issaquah, WA (US); Michael T. Trentalange, Seattle, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,117

(22) Filed: Feb. 5, 2020

(65) Prior Publication Data

US 2020/0172947 A1  Jun. 4, 2020

Related U.S. Application Data

(60) Continuation of application No. 16/191,352, filed on Nov. 14, 2018, which is a division of application No. 15/529,950, filed as application No. PCT/US2015/063271 on Dec. 1, 2015, now Pat. No. 10,167,492.

(60) Provisional application No. 62/085,759, filed on Dec. 1, 2014.

(51) Int. Cl.
*C12P 21/00* (2006.01)
*C07K 16/24* (2006.01)
*A61K 38/00* (2006.01)

(52) U.S. Cl.
CPC .......... *C12P 21/005* (2013.01); *C07K 16/241* (2013.01); *C07K 16/242* (2013.01); *A61K 38/00* (2013.01); *C07K 2317/41* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 4,695,623 A | 9/1987 | Stabinsky |
| 4,897,471 A | 1/1990 | Stabinsky |
| 4,968,607 A | 11/1990 | Dower et al. |
| 5,075,222 A | 12/1991 | Hannum et al. |
| 5,149,792 A | 9/1992 | Thomason et al. |
| 5,272,064 A | 12/1993 | Thomason |
| 5,395,760 A | 3/1995 | Smith et al. |
| 5,610,279 A | 3/1997 | Brockhaus et al. |
| 5,721,121 A | 2/1998 | Etcheverry et al. |
| 5,767,064 A | 6/1998 | Sims et al. |
| 5,856,296 A | 1/1999 | Mosley et al. |
| 5,981,713 A | 11/1999 | Colotta et al. |
| 6,015,938 A | 1/2000 | Boyle et al. |
| 6,096,728 A | 8/2000 | Collins et al. |
| 6,204,363 B1 | 3/2001 | Zsebo et al. |
| 6,235,883 B1 | 5/2001 | Jakobovits et al. |
| 6,271,349 B1 | 8/2001 | Dongall et al. |
| 6,284,471 B1 | 9/2001 | Le et al. |
| 6,337,072 B1 | 1/2002 | Ford et al. |
| 6,544,424 B1 | 4/2003 | Shevitz |
| 7,420,183 B2 | 9/2008 | Kaiser et al. |
| 8,053,238 B2 | 11/2011 | Jin et al. |
| 9,856,502 B2 * | 1/2018 | Nair ........................ C07K 16/00 |
| 2010/0166741 A1 | 1/2010 | Kelley |
| 2012/0164137 A1 | 6/2012 | Sass et al. |
| 2012/0276631 A1 | 11/2012 | Bengea et al. |
| 2013/0303732 A1 | 11/2013 | Hewig, III et al. |
| 2014/0005368 A1 | 1/2014 | Helman et al. |
| 2014/0120581 A1 | 1/2014 | Niwa et al. |
| 2014/0255993 A1 | 9/2014 | Follstad et al. |
| 2015/0119558 A1 | 4/2015 | Song |
| 2015/0344579 A1 | 12/2015 | Thuduppathy et al. |
| 2017/0321240 A1 | 9/2017 | Song |

FOREIGN PATENT DOCUMENTS

| | | |
|---|---|---|
| AU | 588819 B2 | 9/1989 |
| CN | 103397011 A | 11/2013 |
| CN | 103889444 A | 6/2014 |
| EP | 0 367 566 A1 | 5/1990 |
| EP | 0 460 846 A1 | 12/1991 |
| EP | 0 460 846 B1 | 12/1991 |
| EP | 1 498 491 A1 | 1/2005 |
| JP | 2014-505012 A | 2/2014 |
| JP | 2014-520534 A1 | 8/2014 |
| WO | 94/10308 A1 | 5/1994 |
| WO | 94/28391 A1 | 12/1994 |
| WO | 97/01633 A1 | 1/1997 |
| WO | 01/36637 A1 | 5/2001 |
| WO | 01/92337 A2 | 12/2001 |
| WO | 01/92337 A3 | 12/2001 |
| WO | 2008/154014 A2 | 12/2008 |

(Continued)

OTHER PUBLICATIONS

Aggarwal and Gutterman, eds., *Human Cytokines Handbook for Basic and Clinical Research*, All Volumes, Blackwell Sciences, Cambridge, MA (1998) (Table of contents only).
Ausubel et al., *Current Protocols in Molecular Biology*, Green Publishing Associates (1992) (Table of Contents Only).
Brady, L. J. et al., "Molecular Mass Analysis of Antibodies by On-Line SEC-MS," *J. Am. Soc. Mass Spectrom*, 19:502-509 (2008).
Do and Chen-Kiang, "Mechanism of BLyS action in B cell immunity," *Cytokine & Growth Factor Rev.*, 13(1):19-25 (2002).
Furey, J., "Scale-up of a Cell Culture Perfusion Process," *Gen. Eng. News*, 22(7):62 (2002).

(Continued)

*Primary Examiner* — Suzanne M Noakes
(74) *Attorney, Agent, or Firm* — Jonathan M. Dermott

(57) ABSTRACT

The present invention provides a method for manipulating the fucosylated glycan content on a recombinant protein.

24 Claims, 8 Drawing Sheets

(56) References Cited

FOREIGN PATENT DOCUMENTS

| WO | 2008/154014 A3 | 12/2008 |
|---|---|---|
| WO | 2008/157247 A1 | 12/2008 |
| WO | 2012/054654 A2 | 4/2012 |
| WO | 2012/115874 A1 | 8/2012 |
| WO | 2012/145682 A1 | 10/2012 |
| WO | 2013/006479 A2 | 1/2013 |
| WO | 2013/006479 A3 | 1/2013 |
| WO | 2013/040444 A1 | 3/2013 |
| WO | 2013/063298 A1 | 5/2013 |
| WO | 2013/114164 A1 | 8/2013 |
| WO | 2013/114245 A1 | 8/2013 |
| WO | 2013/138159 A1 | 9/2013 |
| WO | 2007/081031 A1 | 7/2019 |

OTHER PUBLICATIONS

Furukawa et al., "β-1, 4-Galactosylation of N-glycans is a complex process," *Biochemica et Biophysica Acta (BBA)*, 1473(1)54-66 (1999).

Gennaro, A. R. et al., *Remington's Pharmaceutical Sciences*, 18$^{th}$ Ed., Mack Publishing Company, Easton, PA (1995) (Table of Contents Only).

Graham et al., "Characteristics of a Human Cell Line Transformed by DNA from Human Adenovirus Type 5," *J. Gen. Virol.*, 36 :59-72 (1977).

Gramer, M. J., "Modulation of Antibody Galactosylation Through Feeding of Uridine, Manganese Chloride, and Glactose," *Biotechnology and Bioengineering*, Wiley & Sons, Hoboken, NJ, US, 108(7):1591-1602 (2011).

Håkansson, K. et al., "Crystal structure of the trimeric α-helical coiled-coil and the three lectin domains of human lung surfactant protein D," *Structure*, 7:255-264 (1999).

Harbury, P. B. et al., Crystal structure of an isoleucine-zipper trimer, *Nature*, 371:80-83 (1994).

Harbury, P. B. et al., "A Switch Between Two-, Three-, and Four-Stranded Coiled Coils in GCN4 Leucine Zipper Mutants," *Science*, 262:1401-1405 (1993).

Harlow and Lane, *Antibodies: A Laboratory Manual*, Cold Spring Harbor Laboratory Press, Cold Spring Harbor, NY (1998) (Table of Contents Only).

Hossler, P. et al., "Optimal and consistent protein glycosylation in mammalian cell culture," *Glycobiology*, 19(9):936-949 (2009).

Houde et al., "Post-translational Modifications Differentially Affect IgG1 Conformation and Receptor Binding," *Molecular and Cellular Proteomics* 9(8):1716-1728 (2010).

Lubiniecki, A. S., ed., *Large Scale Mammalian Cell Culture Technology*, Kaufman, R. J., Author, Chapter 2, "Use of Recombinant DNA Technology for Engineering Mammalian Cells to Produce Proteins,", pp. 15-69 (1990).

Kishimoto, Kikutani et al., eds., Leukocyte Typing VI (Proceedings of the VIth International Workshop and Conference, Kobe, Japan, Nov. 10-12, 1996, Garland Publishing, Inc. (1998) (Table of Contents Only).

Kolkekar, A. S. et al., "Peptidylglycine α-Hydroxylating Monooxygenase: Active Site Residues, Disulfide Linkages, and a Two-Domain Model of the Catalytic Core," *Biochemistry*, 36:10901-10909 (1997).

Liu, S. et al., "Development and Qualification of a Novel Virus Removal Filter for Cell Culture Applications," *Biotechnol. Prog.*, 16:425-434 (2000).

Lovejoy, B. et al., "Crystal Structure of a Synthetic Triple-Stranded α-Helical Bundle," *Science*, 259:1288-1293 (1993).

Maisonpierre, P. C. et al., "Angiopoietin-2, a Natural Antagonist for Tie2 That Disrupts in vivo Angiogenesis," *Science*, 277(5322):55-60 (1997).

Mather, J. P. et al., "Culture of Testicular Cells in Hormone-Supplemented Serum-Free Medium," *Annals NY Acad. Sci.*, 383:44-68 (1982).

Mather, J. P., "Establishment and Characterization of Two Distinct Mouse Testicular Epithelial Cell Lines," *Biol. Reprod.*, 23:243-252 (1980).

McKay, I. and Leigh, I., eds., *Growth Factors: A Practical Approach*, Oxford University Press Inc., New York, NY (1993) (Table of Contents Only).

NCBI Accession No. NM_00682, FGL2.

Pacis, E. et al., "Effects of Cell Culture Conditions on Antibody N-linked Glycosylation—What Affects High Mannose 5 Glycoform," *Biotechnology and Bioengineering*, 108:2348-2358 (2011).

Freshney, R. I. (ed), Richwood, D. and Hames, B. D., Series eds., *Animal Cell Culture: A Practical Approach*, 2$^{nd}$ Edition, Oxford University Press, New York (1992) (Table of Contents Only).

Rüegg, C., "Sequence of a human transcript expressed in T-lymphocytes and encoding a fibrinogen-like protein," *Gene*, 160(2):257-262 (1995).

Sambrook, J. et al., Molecular Cloning, A Laboratory Manual, 4$^{th}$ edition, Cold Spring Harbor Press, Plainview, NY (2012) (Table of Contents Only).

Sambrook, J. et al., *Molecular Cloning: A Laboratory Manual*, 3$^{rd}$ ed., Cold Spring Harbor Laboratory Press, Cold Spring Harbor, NY (2001) (Table of Contents Only).

Shi, H. H. et al., "Recent Advances in the Understanding of Biological Implications and Modulation Methodologies of Monoclonal Antibody N-Linked High Mannos Glycans," *Biotechnology and Bioengineering*, 111(10):1907-1919(2014).

Stettler et al., "New Disposable Tubes for Rapid and Precise Biomass Assessment for Suspension Cultures of Mammalian Cells," *Biotechnol. Bioeng.*, 95(6):1228-1233 (2006).

Thomson, A. W. and Lotze, M. T., eds., *The Cytokine Handbook*, 4$^{th}$ Edition, vols. 1 and 2, Elsevier Science Ltd., Academic Press, San Diego, CA (2003) (Table of Contents Only).

Urlaub, G. et al., "Effects of gamma rays at the dihydrofolate reductase locus: Deletions and inversions," *Somatic Cell and Molecular Genetics*, 12(6):555-556 (1986).

Urlaub, G. and Chasin, L. A., "Isolation of Chinese hamster cell mutants deficient in dihydrofolate reductase activity," *Proc. Natl. Acad. Sci. USA*, 77(7):4216-4220 (1980).

Voisard, D. et al., "Potential of Cell Retention Techniques for Large-Scale High-Density Perfusion Culture of Suspended Mammalian Cells," *Biotechnology and Bioengineering*, 82(7):751-765 (2003).

Kapur et al., "A prominent lack of IgG1-Fc fucosylation of platelet alloantibodies in pregnancy," Blood, 123(4):471-480 (2014); Printed on-line Nov. 15, 2013, doi: 10.1182/blood-2013-09-527978: 10.1182/blood-2013-09-527978.

Kanda, Y., "Comparison of biological activity among nonfucosylated therapeutic IgG1 antibodies with three different N-linked Fc oligosaccharides: the high-mannose, hybrid, and complex types," *Glycobiology*, 17(1):104-118 (2006).

\* cited by examiner

Prediction Profiler for Beta-Galactosylation

Prediction Profiler for Afucosylation

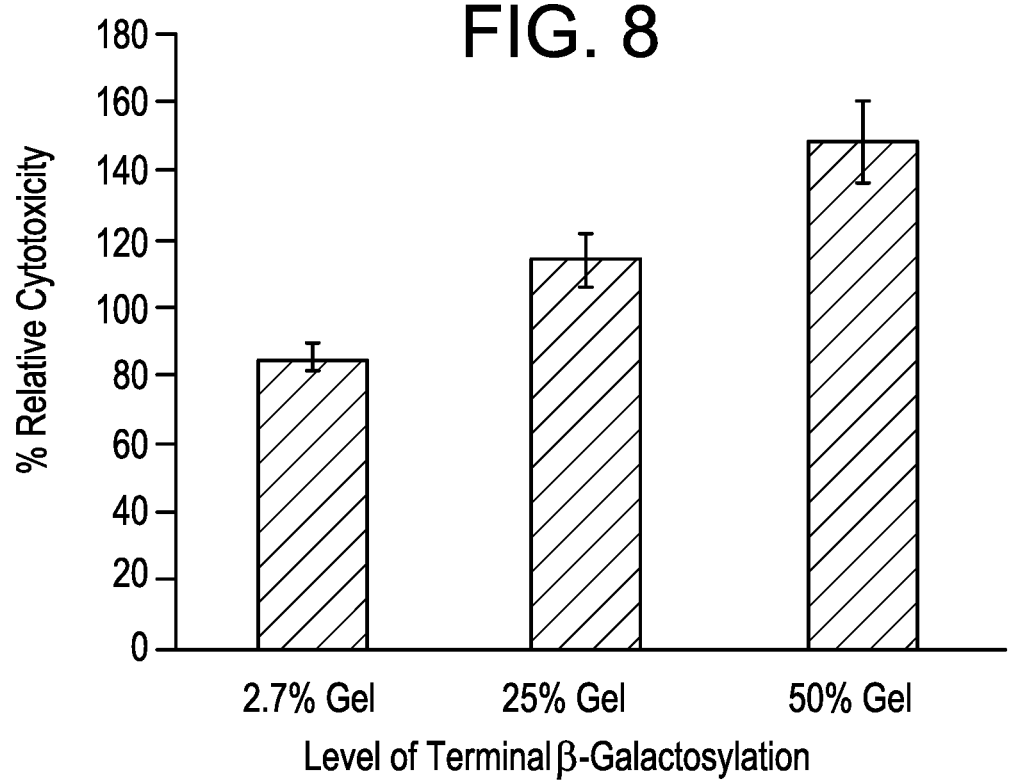

PROCESS FOR MANIPULATING THE LEVEL OF GLYCAN CONTENT OF A GLYCOPROTEIN

This application is a continuation of U.S. application Ser. No. 16/191,352, filed Nov. 14, 2018, which is a divisional of U.S. application Ser. No. 15/529,950, filed May 25, 2017, which is a national stage application under 35 U.S.C. § 371 of International Application No. PCT/US2015/063271, having an international filing date of Dec. 1, 2015, which claims the benefit of U.S. Provisional Patent Application No. 62/085,759, filed on Dec. 1, 2014, which is hereby incorporated by reference in its entirety.

BACKGROUND OF INVENTION

A variety of post-translational modifications including methylation, sulfation, phosphorylation, lipid addition and glycosylation are performed on proteins expressed by higher eukaryotes. Glycosylation involves the covalent attachment of sugar moieties to specific amino acids and is one of the most common and important posttranslational modification for recombinant proteins. Protein glycosylation plays a role in multiple functions, including protein folding and quality control, molecular trafficking and sorting, and cell surface receptor interaction. Many of the secreted proteins, membrane proteins and proteins targeted to vesicles or certain intracellular organelles are known to be glycosylated.

While glycosylation can take many forms, N-linked glycosylation is the most common. N-linked glycosylation involves addition of oligosaccharides to an asparagine residue found in certain recognition sequences in proteins (e.g., Asn-X-Ser/Thr). N-linked glycoproteins contain standard branched structures which are composed of mannose, galactose, N-acetylglucosamine and neuramic acids. N-linked glycosylation of the Fc domain of recombinantly expressed therapeutic antibodies is a critical posttranslational modification. Typical therapeutic antibodies have complex glycoforms possessing fucosylated bi-antennary glycans with a trimannosyl core capped by an N-acetylgalactosamine (GlcNAc), galactose, and N-acetylneuraminic acid (Neu5Ac) residue on each branch. Other glycoforms may be afucosylated, galactosylated, sialylated, have terminal or bisecting GlcNAc, have high mannose (5-9 residues), etc.

Glycosylation can affect therapeutic efficacy of recombinant protein drugs. It is well known that variations in Fc glycosylation can affect Fc-mediated effector functions. Some glycoforms, such as galactosylation and sialylation, are desirable for decreasing immunogenicity, and others, such as afucosylation, bisecting GlcNAc residues, and high mannose glycans, enhance antibody-dependent cellular cytotoxicity (ADCC) activity.

Glycosylation is important in the determination of the structure and function of therapeutic antibodies. It determines binding capabilities and often determines the recognition and processing of the antibody once it is introduced in a therapeutic application. In the case of galactosylation and fucosylation, they determine the complement dependent cytotoxicity (CDC) activity and ADCC functions, respectively, that they influence.

The level of β-galactosylation is related to more "mature" glycoforms. Galactose addition is one of the last stages of glycosylation that takes place in the Golgi apparatus before secretion. Terminal galactose is needed for sialylation, which may be the final step in the glycosylation of some proteins. Galactose also serves as a ligand for galactose binding proteins and is the basis of a variety of antigenic responses which are related to carbohydrate content. Galactose has also been shown to impact the conformation of the protein in solution. (Furukawa and Sato, (1999) Biochimica et Biophysica Acta (BBA), 1473 (1), pages 54-86 and Houde et al., (2010) Molecular and Cellular Proteomics, 9(8), pages 1716-1728.

Fucosylation also takes place in the Golgi apparatus as part of the maturation of the protein prior to secretion. If a protein is fucosylated it typically happens before galactosylation in the glycosylation pathway. However, fucosylation is not necessary for galactosylation to proceed (Hossler et al., (2009)_Glycobiology, 19(9), pages 936-949).

The influence of glycosylation on bioactivity, pharmacokinetics, immunogenicity, solubility and in vivo clearance of therapeutic glycoproteins have made monitoring and control of glycosylation a critical parameter for biopharmaceutical manufacturing. Therefore, methods for manipulating the level of glycan content of therapeutic proteins would be beneficial.

There is a need in the pharmaceutical industry to manipulate and control the level of glycan content of recombinant therapeutic glycoproteins and methods for accomplishing such without significant impact on cell growth, viability and productivity would be useful. The invention provides a method for manipulating the fucosylated glycan content on a recombinant protein by regulating copper and manganese content and pH in cell culture medium.

SUMMARY OF THE INVENTION

The invention provides a method for manipulating the fucosylated glycan content on a recombinant protein comprising inoculating a bioreactor with host cells expressing the recombinant protein, culturing the host cells in a serum free, chemically defined cell culture medium; wherein the cell culture medium includes from 10 to 100 ppb copper and from 50 to 1000 nM manganese, at pH 7.0, harvesting the recombinant protein produced by the host cell, wherein the level of afucosylated glycans on the recombinant protein increases compared to the afucosylated glycan level obtained in the same cell culture medium at a lower pH.

In one embodiment the method further comprising an increase in the level of β-galactosylation on the recombinant protein.

In one embodiment the concentration of coper is 100 ppb.

In one embodiment the concentration of manganese is 1000 nM.

In one embodiment the fucosylated glycan content is manipulated to influence the effector function of the recombinant protein.

In one embodiment the method further comprising a temperature shift. In a related embodiment the temperature shift is from 36° C. to 31° C. In another related embodiment the temperature shift occurs at the transition between the growth phase and production phase. In yet another related embodiment the temperature shift occurs during the production phase.

In one embodiment the host cell expressing the recombinant protein is cultured in a batch culture, fed-batch culture, perfusion culture, or combinations thereof. In a related embodiment the culture is a perfusion culture. In another related embodiment perfusion comprises continuous perfusion. In another related embodiment rate of perfusion is constant. In another related embodiment the perfusion is performed at a rate of less than or equal to 1.0 working volumes per day. In yet another related the perfusion is accomplished by alternating tangential flow.

In one embodiment the bioreactor has a capacity of at least 500 L.

In one embodiment the bioreactor has a capacity of at least 500 L to 2000 L.

In one embodiment the bioreactor has a capacity of at least 1000 L to 2000 L.

In one embodiment the bioreactor is inoculated with at least $0.5 \times 10^6$ cells/mL.

In one embodiment the serum-free chemically defined cell culture medium is a perfusion cell culture medium.

In one embodiment the host cells are mammalian cells.

In one embodiment the host cells are Chinese Hamster Ovary (CHO) cells.

In one embodiment the recombinant protein is a glycoprotein.

In one embodiment the recombinant protein is selected from the group consisting of a human antibody, a humanized antibody, a chimeric antibody, a recombinant fusion protein, or a cytokine.

In one embodiment the recombinant protein produced by the host cell is purified and formulated into a pharmaceutically acceptable formulation.

In one embodiment is a recombinant protein produced by the method of the invention. In a related embodiment the recombinant protein according is purified. In yet another related embodiment the recombinant protein is formulated into a pharmaceutically acceptable formulation.

By the day 17 the cultures at pH 6.85 had higher final viability compared to cultures run at pH 7.0. However, final viability was over 80%, regardless of pH. Copper and manganese concentration in the ranges tested had no effect on viability.

Figure 1:
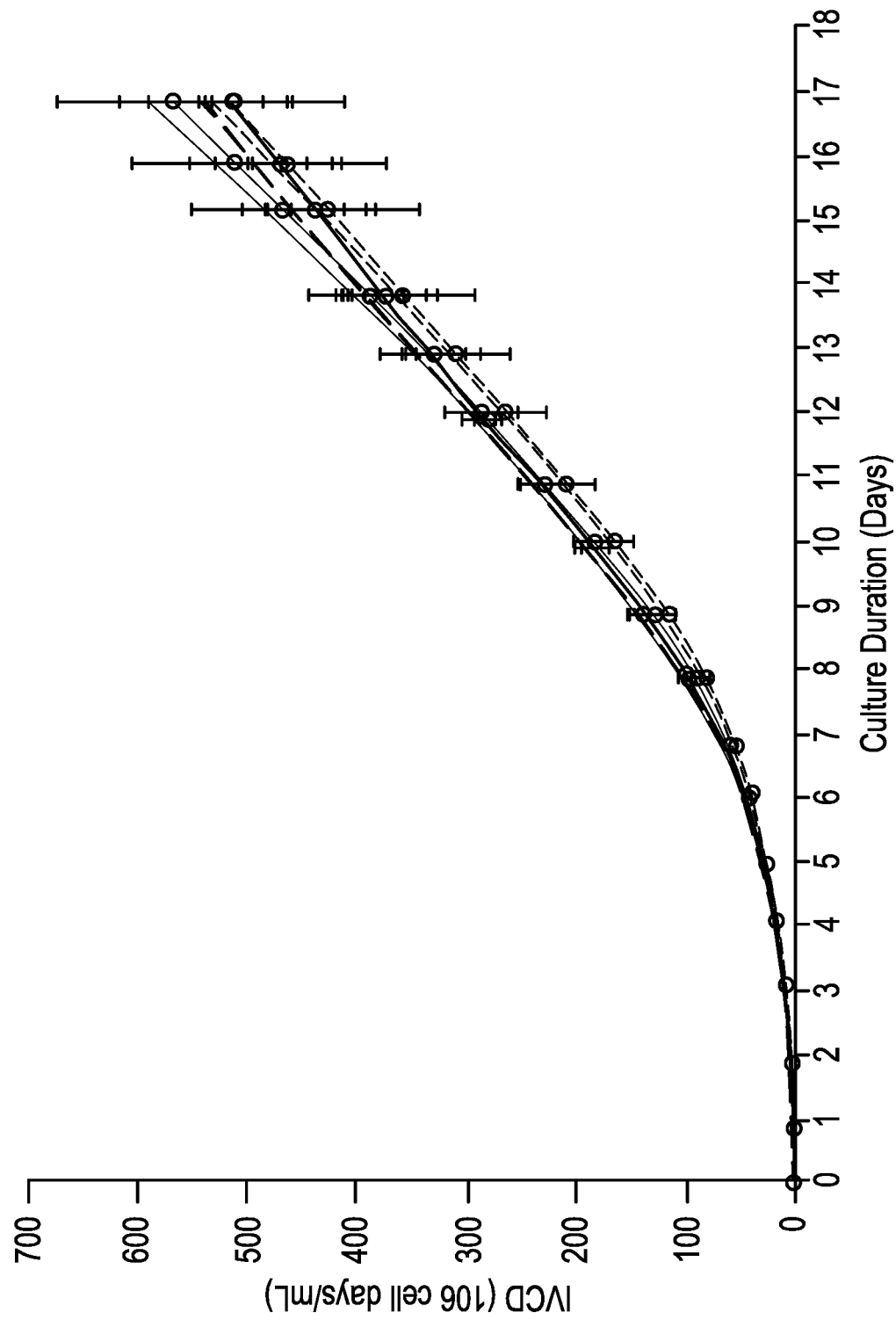
FIG. 1 Integrated Viable Cell Density ($10^6$ cell days/ml)
pH 6.85 50 $Mn^{2+}$ 10 $Cu^{2+}$ (gray dashed line with +)
pH 6.85 50 $Mn^{2+}$ 100 $Cu^{2+}$ (gray line with +)
pH 6.85 1000 $Mn^{2+}$ 10 $Cu^{2+}$ (gray dashed line with open circle)
pH 6.85 50 $Mn^{2+}$ 100 $Cu^{2+}$ (gray line with open circle)
pH 7.0 50 $Mn^{2+}$ 10 $Cu^{2+}$ (black dashed line with +)
pH 7.0 50 $Mn^{2+}$ 100 $Cu^{2+}$ (black line with +)
pH 7.0 1000 $Mn^{2+}$ 10 $Cu^{2+}$ (black dashed line with open circle)
pH 7.0 50 $Mn^{2+}$ 100 $Cu^{2+}$ (black line with open circle)
pH appeared to be the only factor impacting cell growth. Concentrations of manganese and copper seemed to have no effect on cell growth.
Figure 2:
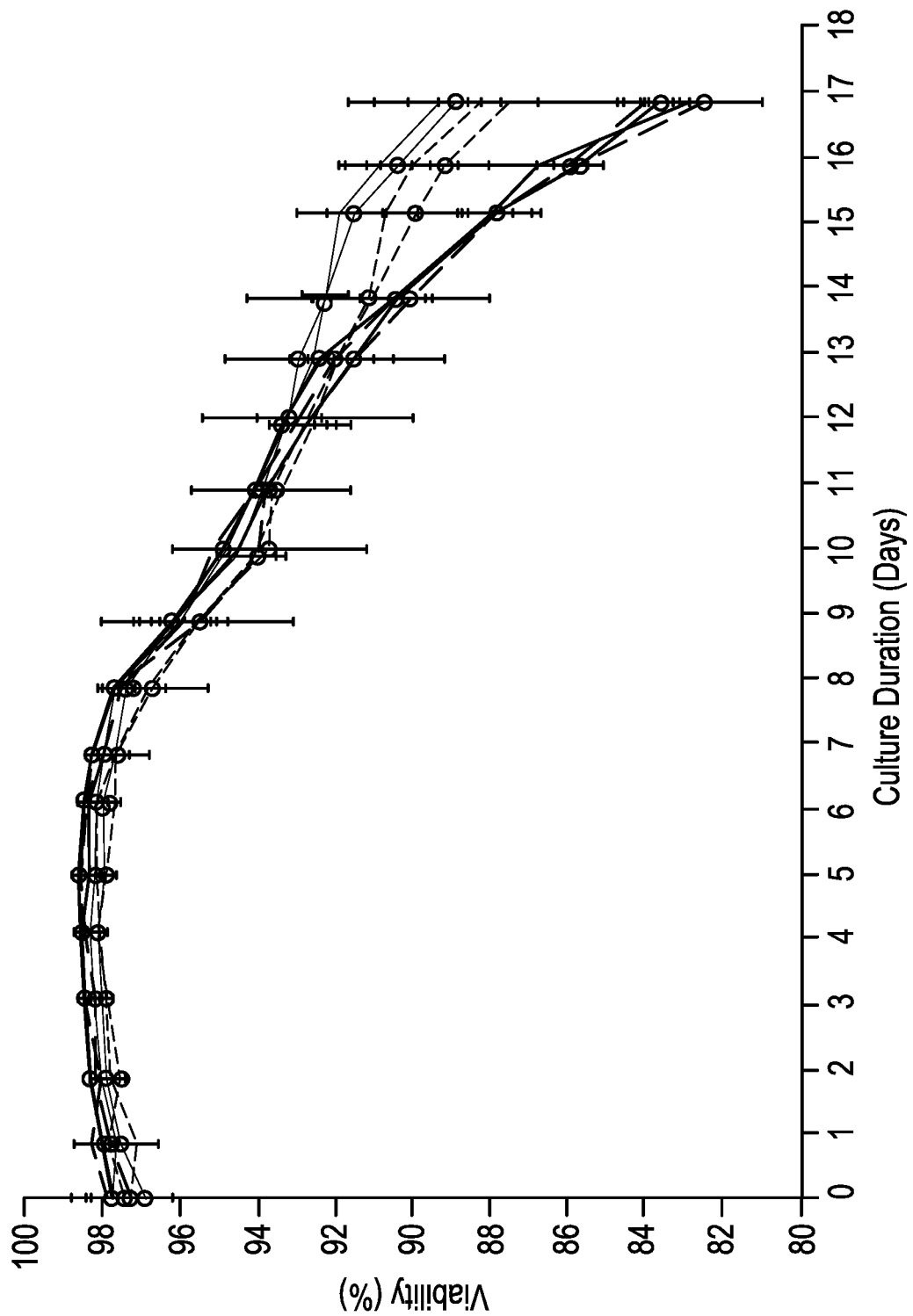
FIG. 2 Viability (%)
pH 6.85 50 $Mn^{2+}$ 10 $Cu^{2+}$ (gray dashed line with +)
pH 6.85 50 $Mn^{2+}$ 100 $Cu^{2+}$ (gray line with +)
pH 6.85 1000 $Mn^{2+}$ 10 $Cu^{2+}$ (gray dashed line with open circle)
pH 6.85 50 $Mn^{2+}$ 100 $Cu^{2+}$ (gray line with open circle)
pH 7.0 50 $Mn^{2+}$ 10 $Cu^{2+}$ (black dashed line with +)
pH 7.0 50 $Mn^{2+}$ 100 $Cu^{2+}$ (black line with +)
pH 7.0 1000 $Mn^{2+}$ 10 $Cu^{2+}$ (black dashed line with open circle)
pH 7.0 50 $Mn^{2+}$ 100 $Cu^{2+}$ (black line with open circle)
Figure 3:
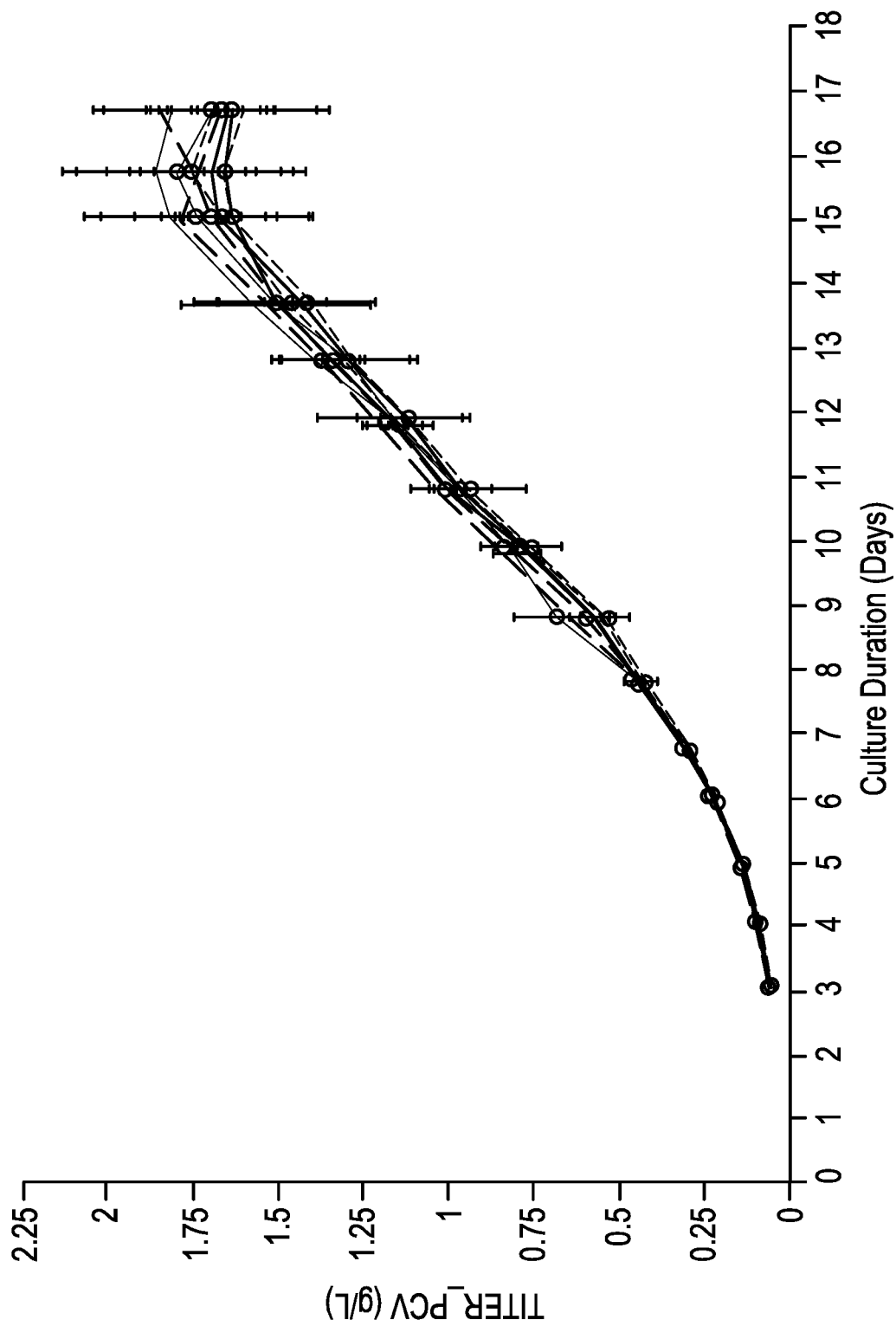

FIG. 3 Packed cell adjusted titer (g/L)
pH 6.85 50 $Mn^{2+}$ 10 $Cu^{2+}$ (gray dashed line with +)
pH 6.85 50 $Mn^{2+}$ 100 $Cu^{2+}$ (gray line with +)
pH 6.85 1000 $Mn^{2+}$ 10 $Cu^{2+}$ (gray dashed line with open circle)
pH 6.85 50 $Mn^{2+}$ 100 $Cu^{2+}$ (gray line with open circle)
pH 7.0 50 $Mn^{2+}$ 10 $Cu^{2+}$ (black dashed line with +)
pH 7.0 50 $Mn^{2+}$ 100 $Cu^{2+}$ (black line with +)
pH 7.0 1000 $Mn^{2+}$ 10 $Cu^{2+}$ (black dashed line with open circle)
pH 7.0 50 $Mn^{2+}$ 100 $Cu^{2+}$ (black line with open circle)

pH appears to have no statistical impact on packed cell adjusted titer, likewise, copper and manganese concentration had no effect on this cell line and process.

Figure 4:
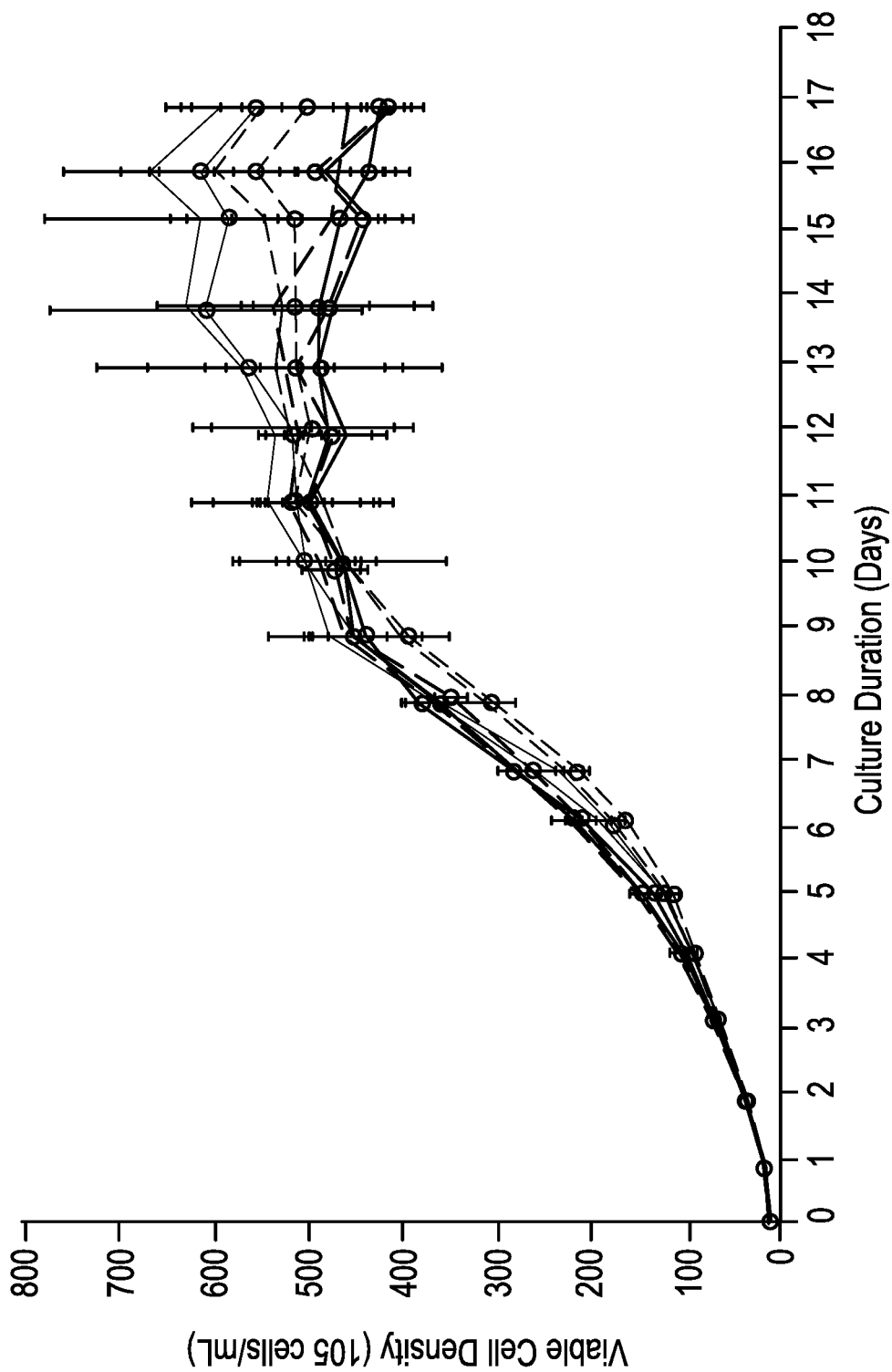

FIG. 4 Viable Cell Density ($10^5$ cell days/ml)
pH 6.85 50 Mn 10 Cu (gray dashed line with +)
pH 6.85 50 Mn 100 Cu (gray line with +)
pH 6.85 1000 Mn 10 Cu (gray dashed line with open circle)
pH 6.85 50 $Mn^{2+}$ 100 $Cu^{2+}$ (gray line with open circle)
pH 7.0 50 $Mn^{2+}$ 10 $Cu^{2+}$ (black dashed line with +)
pH 7.0 50 $Mn^{2+}$ 100 $Cu^{2+}$ (black line with +)
pH 7.0 1000 $Mn^{2+}$ 10 $Cu^{2+}$ (black dashed line with open circle)
pH 7.0 50 $Mn^{2+}$ 100 $Cu^{2+}$ (black line with open circle)

Reactors run at pH 6.85 grew to cell densities of nearly $10^6$ cells per mL more than reactors grown at pH 7.0. Concentration of copper and manganese had no statistically significant effect on cell growth in this experiment for this cell line and process. pH was the only factor impacting cell growth.

Figure 5:
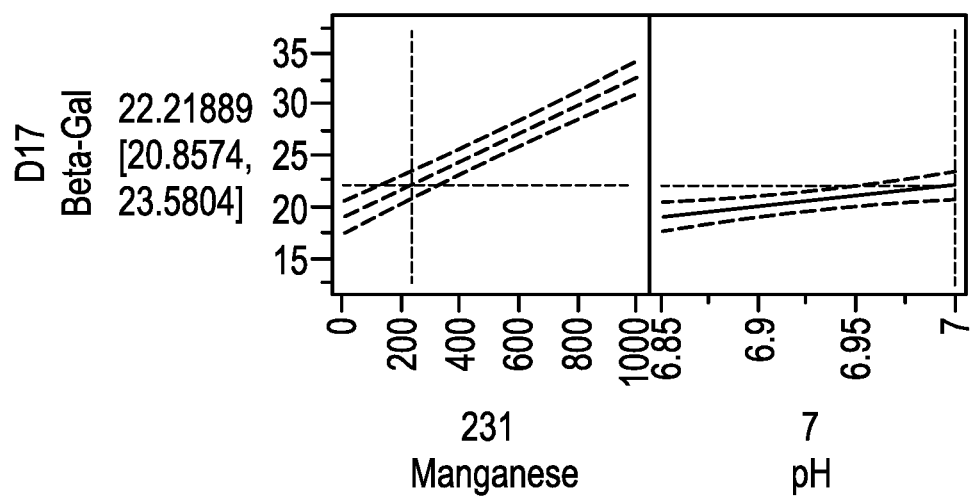

FIG. 5 β-Galactosylation (Adj. $R^2$=0.95) Prediction profiler generated using JMP statistical software. The profile illustrates the directionality and magnitude of the changes in β-galactosylation as a result of manipulating pH and manganese concentration. The terms in the profiler represent the remaining terms in the statistical model after removing those terms that were not statistically significant. The addition of manganese had a significant effect on the level of beta-galactosylation; the greater the concentration of manganese, the greater the percentage of beta-galactosylation. pH also had a statistically significant effect on beta-galactosylation, as pH increased, beta-galactosylation also increased, but not to the extent observed when manganese was added.

Figure 6:
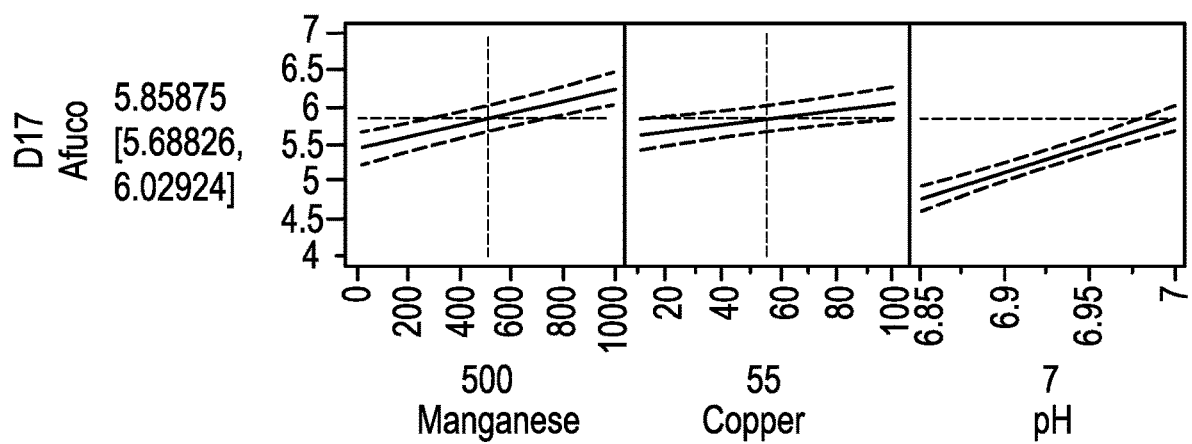

FIG. 6 Afucosylation (Adj. $R^2$=0.92) Prediction profiler generated using JMP statistical software. The profile illustrates the directionality and magnitude of the changes in afucosylation as a result of manipulating pH, manganese and copper concentrations. The terms in the profiler represent the remaining terms in the statistical model after removing those terms that were not statistically significant. Copper, manganese and pH all had a statistically significant impact on the afucosylation levels. Increasing levels of copper and manganese, as well as increasing pH, all resulted in an increase in afucosylation.

Figure 7:
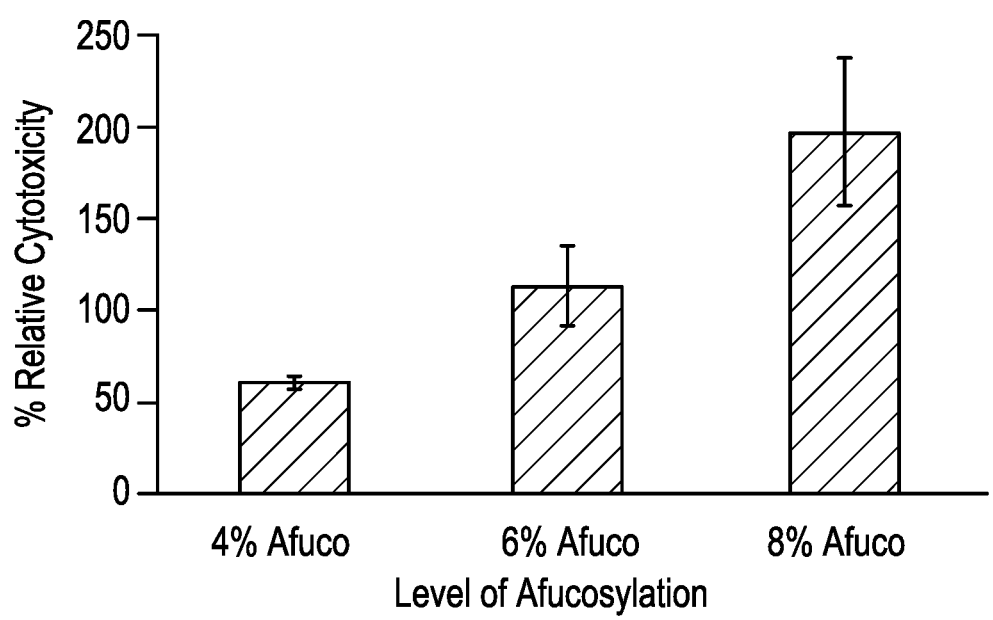

FIG. 7 ADCC relative cytotoxicity, at base afucosylation (4%), 6% afucosylation and 8% afucosylation.

FIG. 8 CDC scaled dose response, at base β-galactosylation, (2.7%), 25% β-galactosylation and 50% β-galactosylation.

DETAILED DESCRIPTION OF THE INVENTION

Varying the concentration of manganese in cell culture medium can influence the degree of β-galactosylation of recombinant antibodies. Manganese acts as a cofactor in the modulation of the activity of galactosyltransferase. The galactosyltransferase mediated reaction employs UDP-galactose as the sugar substrate and manganese as the cofactor. A change in the level of galactosylation can be caused by a change in the UDP-galactose availability or a change in the enzymatic activity (for example, by altering the manganese cofactor concentration), or both.

Analogously, fucosylation may be moderated by altering the levels of the GDP-fucose substrate, by interfering with the activity of fucosyltransferase or by modifying the GDP-fucose transporter mechanism. However, metal ions have not been reported to play a direct role in any of these mechanisms. As described herein, increasing the level of manganese and copper was found to impact recombinant protein fucosylated glycan content by significantly increasing the level of afucosylated glycans. In addition it was found that pH also played a major role in determining glycosylation patterns.

The type and extent of N-linked glycosylation on IgG1 antibodies are known to affect Fc-mediated effector functions. For example, the level of afucosylation strongly enhances antibody dependent cell mediated cytotoxicity (ADCC) by increasing binding affinity to Fcγ receptors, whereas the level of galactosylation can influence complement dependent cytotoxicity (CDC) activity. This makes it critical to understand and control the nature and level of glycosylation of therapeutic proteins.

As described herein, the enhancement of afucosylation and galactosylation had substantial impact on ADCC and CDC effector A method is provided to improve control of the levels of afucosylated glycans on a recombinant protein by manipulating the pH and the concentrations of manganese ($Mn^{2+}$) and copper ($Cu^{2+}$) in a cell culture medium. The levels of afucosylated and β-galactosylated glycans were increased without impacting cell culture performance.

The invention provides a method for manipulating the fucosylated glycan content on a recombinant protein comprising inoculating a bioreactor with host cells expressing the recombinant protein, culturing the host cells in a serum free, chemically defined cell culture medium; wherein the cell culture medium includes from 10 to 100 ppb copper and from 50 to 1000 nM manganese, at pH 7.0, harvesting the recombinant protein produced by the host cell, wherein the level of afucosylated glycans on the recombinant protein increases compared to the afucosylated glycan level obtained in the same cell culture medium at a lower pH. In one embodiment the method further comprising an increase in the level of β-galactosylation on the recombinant protein. In one embodiment the concentration of copper is 100 ppb. In one embodiment the concentration of manganese is 1000 nM. In one embodiment the fucosylated glycan content is manipulated to influence the effector function of the recombinant protein.

In one embodiment the method further comprising a temperature shift. In a related embodiment the temperature shift is from 36° C. to 31° C. In another related embodiment the temperature shift occurs at the transition between the growth phase and production phase. In yet another related embodiment the temperature shift occurs during the production phase.

In one embodiment the host cell expressing the recombinant protein is cultured in a batch culture, fed-batch culture, perfusion culture, or combinations thereof. In a related embodiment the culture is a perfusion culture. In another related embodiment perfusion comprises continuous perfusion. In another related embodiment rate of perfusion is constant. In another related embodiment the perfusion is performed at a rate of less than or equal to 1.0 working volumes per day. In yet another related embodiment the perfusion is accomplished by alternating tangential flow.

In one embodiment the bioreactor has a capacity of at least 500 L. In one embodiment the bioreactor has a capacity of at least 500 L to 2000 L. In one embodiment the bioreactor has a capacity of at least 1000 L to 2000 L. In one embodiment the bioreactor is inoculated with at least 0.5× $10^6$ cells/mL.

In one embodiment the serum-free chemically defined cell culture medium is a perfusion cell culture medium. In one embodiment the host cells are mammalian cells. In one embodiment the host cells are Chinese Hamster Ovary (CHO) cells.

In one embodiment the recombinant protein is a glycoprotein. In one embodiment the recombinant protein is selected from the group consisting of a human antibody, a humanized antibody, a chimeric antibody, a recombinant fusion protein, or a cytokine. In one embodiment the recombinant protein produced by the host cell is purified and formulated into a pharmaceutically acceptable formulation. In one embodiment is a recombinant protein produced by the method of the invention. In a related embodiment the recombinant protein according is purified. In yet another related embodiment the recombinant protein is formulated into a pharmaceutically acceptable formulation.

Cell Culture

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate.

As used herein, the terms "cell culturing medium" (also called "culture medium", "cell culture media", "tissue culture media") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

The nutrient solution may optionally be supplemented with additional components to optimize growth of cells, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal protein (peptone or peptone mixtures, which can be obtained from animal byproducts, purified gelatin or plant material); antibiotics, e.g., gentamycin; cell protectants or surfactants, polyamines, e.g., putrescine, spermidine or spermine (see e.g., WIPO Publication No. WO 2008/154014) and pyruvate (see e.g. U.S. Pat. No. 8,053,238) depending on the requirements of the cells to be cultured and/or the desired cell culture parameters.

Non-ionic surfactants may also be added to the cell culture medium. Examples of non-ionic surfactants include, but are not limited to, polyvinyl alcohol, polyethylene glycol, and non-ionic block copolymer surfactants. Also included are alkyl poly(ethylene oxide), copolymers of poly(ethylene oxide) and poly(propylene oxide) (EO-PO block copolymers), poly(vinylpyrrolidone), alkyl polyglucosides (such as sucrose monostearate, lauryl diglucoside, or sorbitan monolaureate, octyl glucoside and decyl maltoside), fatty alcohols (cetyl alcohol or olelyl alcohol), or cocamides (cocamide MEA, cocamide DEA and cocamide TEA).

Also included are block copolymers based on ethylene oxide and propylene oxide, also referred to as polyoxypropylene-polyoxyethylene block copolymers. These molecules are nonionic triblock copolymers having a central hydrophobic chain of polyoxypropylene (poly(propylene oxide)) flanked by two hydrophilic chains of polyoxyethylene (poly(ethylene oxide)). Of particular interest are those having 70 polyoxypropylene units and 30 units of each of the polyoxyethylene chains. In a preferred embodiment the block copolymer is poloxamer 188 (CAS #90003-11-6 with an average molecular weight of 8.4 kd, BASF Chemical, Washington, N.J.) which is sold under various brand names such as Pluronic® F68, Kolliphor® P-188, Lutrol® F68, and Lutrol® 188. Such non-ionic surfactants may be added at concentrations up to 5 g/L or more and may be used to maintain cell viability for longer culture durations under ATF perfusion conditions.

The present invention provides a cell culture medium that contains from 10 to 100 ppb copper and from 50 to 1000 nM manganese. In one embodiment the cell culture medium contains 100 ppb manganese. In another embodiment the cell culture medium contains 1000 nM manganese. In another embodiment the cell culture medium contains 100 ppb manganese and 1000 nM manganese. Copper and manganese salts useful for this invention include, but are not limited to, cupric sulfate pentahydrate and manganese sulfate monohydrate.

Cell culture medium components, including copper and manganese, may be completely milled into a powder medium formulation; partially milled with liquid supplements added to the cell culture medium as needed; or cell culture medium components may be added in a completely liquid form to the cell culture.

Cell culture medium include those that are typically employed in and/or are known for use with any cell culture process, such as, but not limited to, batch, extended batch, fed-batch and/or perfusion or continuous culturing of cells.

A "base" (or batch) cell culture medium refers to a cell culture medium that is typically used to initiate a cell culture and is sufficiently complete to support the cell culture.

A "growth" cell culture medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium refers to a cell culture medium that is typically used in cell cultures during the transition and production phases when exponential growth is ending and protein production takes over, and is sufficiently complete to maintain a desired cell density, viability and/or product titer during these phases.

A "perfusion" cell culture medium refers to a cell culture medium that is typically used in cell cultures that are maintained by perfusion or continuous culture methods and is sufficiently complete to support the cell culture during this process.

Perfusion cell culture medium formulations may be enriched or more concentrated than base cell culture medium formulations to accommodate for the method used to remove the spent medium. Perfusion cell culture medium can be used during both the growth and production phases.

Cell cultures can be supplemented with concentrated feed medium containing components, such as nutrients and amino acids, which are consumed during the course of the production phase of the culture. Concentrated cell culture medium can contain some or all of the nutrients necessary to maintain the cell culture; in particular, concentrated medium can contain nutrients identified as or known to be consumed during the course of the production phase of the cell culture. Concentrated medium may be based on just about any cell culture media formulation. Such a concentrated feed medium can contain some or all the components of the cell culture medium at, for example, about 2×, 3×, 4×, 5×, 6×, 7×, 8×, 9×, 10×, 12×, 14×, 16×, 20×, 25×, 30×, 40×, 50×, 75×, 100×, 200×, 400×, 600×, 800×, or even 1000× of their normal amount.

Cell culture medium, in certain embodiments, may be serum-free and/or free of products or ingredients of animal origin. Cell culture medium, in certain embodiments, may be chemically defined, where all of the chemical components are known.

As is appreciated by the practitioner, animal or mammalian cells are cultured in a medium suitable for the particular cells being cultured and which can be determined by the person of skill in the art without undue experimentation. Commercially available media can be utilized and include, but is not limited to, Iscove's Modified Dulbecco's Medium, RPMI 1640, and Minimal Essential Medium-alpha. (MEM-alpha), Dulbecco's Modification of Eagle's Medium (DMEM), DME/F12, alpha MEM, Basal Medium Eagle with Earle's BSS, DMEM high Glucose, with Glutamine, DMEM high glucose, without Glutamine, DMEM low Glucose, without Glutamine, DMEM:F12 1:1, with Glutamine, GMEM (Glasgow's MEM), GMEM with glutamine, Grace's Complete Insect Medium, Grace's Insect Medium, without FBS, Ham's F-10, with Glutamine, Ham's F-12, with Glutamine, IMDM with HEPES and Glutamine, IMDM with HEPES and without Glutamine, IP41 Insect Medium, 15 (Leibovitz)(2×), without Glutamine or Phenol Red, 15 (Leibovitz), without Glutamine, McCoy's 5A Modified Medium, Medium 199, MEM Eagle, without Glutamine or Phenol Red (2×), MEM Eagle-Earle's BSS, with glutamine, MEM Eagle-Earle's BSS, without Glutamine, MEM Eagle-Hanks BSS, without Glutamine, NCTC-109, with Glutamine, Richter's CM Medium, with Glutamine, RPMI 1640 with HEPES, Glutamine and/or Penicillin-Streptomycin, RPMI 1640, with Glutamine, RPMI 1640, without Glutamine, Schneider's Insect Medium or any other media known to one skilled in the art, which are formulated for particular cell types. To the foregoing exemplary media can be added supplementary components or ingredients, including optional components, in appropriate concentrations or amounts, as necessary or desired, and as would be known and practiced by those having in the art using routine skill.

Cell cultures can also be supplemented with independent concentrated feeds of particular nutrients which may be difficult to formulate or are quickly depleted in cell cultures. Such nutrients may be amino acids such as tyrosine, cysteine and/or cystine (see e.g., WIPO Publication No. 2012/145682). For example, a concentrated solution of tyrosine may be independently fed to a cell culture grown in a cell culture medium containing tyrosine. A concentrated solution of tyrosine and cystine may also be independently fed to the cell culture being grown in a cell culture medium lacking tyrosine, cystine and/or cysteine. The independent feeds can begin prior to or at the start of the production phase. The independent feeds can be accomplished by fed batch to the cell culture medium on the same or different days as the concentrated feed medium. The independent feeds can also be perfused on the same or different days as the perfused medium.

Methods can be employed to continuous feed a mammalian cell culture, such as those that do not employ feedback control (see WIPO Publication No. WO 2013/040444).

Media Treatments

The cell culture medium can be treated using methods or devices to sterilize or disinfect media prior to addition to the bioreactor and/or cell culture. Cell culture media may be treated using high temperature short time (HTST) (see, e.g., U.S. Pat. No. 7,420,183). Cell culture media may also be treated using UV in combination with filtration (see, e.g., WIPO Publications WO 2008/157247; WO 2012/115874; WO 2013/063298 and WO 2013/138159). Cell culture media may be subjected to nanofiltration (see, e.g., Liu et al., (2000) Biotechnol. Prog. 16:425-434). Cell culture media may be treated with chemicals that inactivate viruses, such as solvents, detergents, psoralen, or beta-propiolactone.

Cells

Cell lines (also referred to as "host cells") used in the invention are genetically engineered to express a polypeptide of commercial or scientific interest. Cell lines are typically derived from a lineage arising from a primary culture that can be maintained in culture for an unlimited time. The cells can contain introduced, e.g., via transformation, transfection, infection, or injection, expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in J. Sambrook et al., 2012, *Molecular Cloning, A Laboratory Manual*, 4$^{th}$ edition Cold Spring Harbor Press, Plainview, N.Y. or any of the previous editions; F. M. Ausubel et al., 2013, *Current Protocols in Molecular Biology*, John Wiley & Sons, New York, N.Y, or any of the previous editions; Kaufman, R. J., *Large Scale Mammalian Cell Culture*, 1990, all of which are incorporated herein for any purpose.

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or other factors, such as those described herein. The cells are typically selected that can express and secrete proteins, or that can be molecularly engineered to express and secrete, large quantities of a particular protein, more particularly, a glycoprotein of interest, into the culture medium. It will be understood that the protein produced by a host cell can be endogenous or homologous to the host cell. Alternatively, the protein is heterologous, i.e., foreign, to the host cell, for example, a human protein produced and secreted by a Chinese hamster ovary (CHO) host cell. Additionally, mammalian proteins, i.e., those originally obtained or derived from a mammalian organism, are attained by the methods the present invention and can be secreted by the cells into the culture medium.

The method of the present invention can be used in the culture of a variety of cells. In one embodiment, the cultured cells are eukaryotic cells such as plant and/or animal cells. The cells can be mammalian cells, fish cells, insect cells, amphibian cells or avian cells. A wide variety of mammalian cell lines suitable for growth in culture are available from the American Type Culture Collection (Manassas, Va.) and other depositories as well as commercial vendors. Cell that can be used in the processes of the invention include, but not limited to, MK2.7 cells, PER-C6 cells, Chinese hamster ovary cells (CHO), such as CHO-K1 (ATCC CCL-61), DG44 (Chasin et al., 1986, *Som. Cell Molec. Genet.*, 12:555-556; Kolkekar et al., 1997, *Biochemistry*, 36:10901-10909; and WO 01/92337 A2), dihydrofolate reductase negative CHO cells (CHO/-DHFR, Urlaub and Chasin, 1980, *Proc. Natl. Acad. Sci. USA*, 77:4216), and dpl2.CHO cells (U.S. Pat. No. 5,721,121); monkey kidney cells (CV1, ATCC CCL-70); monkey kidney CV1 cells transformed by SV40 (COS cells, COS-7, ATCC CRL-1651); HEK 293 cells, and Sp2/0 cells, 5 L8 hybridoma cells, Daudi cells, EL4 cells, HeLa cells, HL-60 cells, K562 cells, Jurkat cells, THP-1 cells, Sp2/0 cells, primary epithelial cells (e.g., keratinocytes, cervical epithelial cells, bronchial epithelial cells, tracheal epithelial cells, kidney epithelial cells and retinal epithelial cells) and established cell lines and their strains (e.g., human embryonic kidney cells (e.g., 293 cells, or 293 cells subcloned for growth in suspension culture, Graham et al., 1977, *J. Gen. Virol.*, 36:59); baby hamster kidney cells (BHK, ATCC CCL-10); mouse sertoli cells (TM4, Mather, 1980, *Biol. Reprod.*, 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.*, 383:44-68); MCR 5 cells; FS4 cells; PER-C6 retinal cells, MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS—C—I cells, LLC-MK$_2$ cells, Clone M-3 cells, 1-10 cells, RAG cells, TCMK-1 cells, Y-1 cells, LLC-PKi cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCli cells, CV-1 cells, COS-1 cells, COS-3 cells, COS-7 cells, African green monkey kidney cells (VERO-76, ATCC CRL-1587; VERO, ATCC CCL-81); DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, $HSDM_1C_3$ cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntac cells, SIRC cells, $C_{II}$ cells, and Jensen cells, or derivatives thereof) or any other cell type known to one skilled in the art.

Cells may be suitable for adherent, monolayer or suspension culture, transfection, and expression of proteins, for example, antibodies. The cells can be used with batch, fed batch and perfusion or continuous culture methods.

Types of Cell Cultures

For the purposes of understanding, yet without limitation, it will be appreciated by the skilled practitioner that cell cultures and culturing runs for protein production can include three general types; namely, batch or extended batch culture, fed-batch culture, perfusion culture, or combinations thereof. In batch culture, cells are initially cultured in medium and this medium is not removed, replaced, or supplemented, i.e., the cells are not "fed" with fresh medium, during or before the end of the culturing run. The desired product is harvested at the end of the culturing run.

For fed-batch cultures, the culturing run time is increased by supplementing the culture medium one or more times (or continuously) with fresh medium during the run, i.e., the cells are "fed" with new medium ("fed medium") during the culturing period. Fed-batch cultures can include the various feeding regimens and times, for example, daily, every other day, every two days, etc., more than once per day, or less than once per day, and so on. Further, fed-batch cultures can be fed continuously with feeding medium. The desired product may then be harvested at the end of the culturing/ production run.

Perfusion culture, sometimes referred to as continuous culture, is one in which the cell culture receives fresh perfusion medium, and where spent medium is removed from the bioreactor during the run. Perfusion of fresh media into the cell culture and removal of spend media can be continuous, step-wise, intermittent, or a combination of any or all of these. Perfusion rates can range from less than one working volume per day to many working volumes per day.

The term "perfusion flow rate" is the amount of media that is passed through (added and removed) from a bioreactor, typically expressed as some portion of or a multiple of the working volume, in a given time. The perfusion flow rate may vary over the duration of the cell culture run. "Working volume" refers to the amount of bioreactor volume used for cell culture. In one embodiment the perfusion flow rate is less than or equal to one working volume per day. Perfusion feed medium can be formulated to maximize perfusion nutrient concentration to minimize perfusion rate.

Preferably the cells are retained in the culture and the spent medium that is removed is substantially free of cells or has significantly fewer cells than the culture. Recombinant proteins expressed by the cell culture can also be retained in the culture for later harvest or removed with the spent medium.

Perfusion can be accomplished by a number of means including centrifugation, sedimentation, or filtration, See e.g. Voisard et al., (2003), Biotechnology and Bioengineering 82:751-65. In one embodiment a filtration method is used. Filters include membrane filters, ceramic filters and metal filters and may be in any shape, including spiral wound or tubular or in the form of a sheet. One or more filters can be connected to, in fluid communication with, a bioreactor together or independently, in series or in parallel.

Hollow fiber filters may be used in mammalian cell perfusion culture for cell and/or recombinant protein retention. When the cell culture, including cell culture media, cells (whole and lysed), soluble expressed recombinant proteins, host cell proteins, waste products and the like, are introduced to the filter, depending on the pore size or molecular weight cutoff (MWCO) the hollow fiber material may retain certain cell culture components on the lumen side (inside) and allow certain components to pass through the filter (permeate) based on the pore size or molecular weight cutoff of the hollow fiber material. The material that is retained (retentate) is returned to the bioreactor. Fresh perfusion cell culture media is added to the bioreactor and permeate is withdrawn from the filter at predetermined intervals or continuously to maintain a desired or constant bioreactor volume. The permeate can be discarded, stored in holding tanks, bags or totes or transferred directly to another unit operation, such as filtration, flocculation, centrifugation and/or other downstream purification methods or the like. Hollow fibers for microfiltration typically have a pore size ranging from 0.1 µm to 5-10 µm or a molecular weight cut off of 500 kDa or more and can be used to allow the protein to pass through into the permeate. Ultrafiltration hollow fibers typically have a pore size range of 0.01 µm to 0.1 µm or a molecular weight cut off of 300 kDa or less, and can be used to retain the desired protein in the retentate and return it back to the bioreactor. This can be used, for example, to concentrate the recombinant protein product for harvest. Such filters are available commercially, such as Xampler UFP-750-E-4MA, Xampler UFP-30-E-4MA, (GE Healthcare, Pittsburgh, Pa.) and Midikros TC Modules T02-E030-10, T02-050-10, T02-E750-05, T02-M10U-06 (Spectrum Laboratories, Inc, Dominguez, Calif.).

The cell culture may be drawn out of the bioreactor and into the filter by a pumping system, which passes the cell culture through the lumen side of the hollow fiber. Examples of cell pumping systems include peristaltic pumps, double diaphragm pumps, low shear pumps (Levitronix® pumps, Zurich, Switzerland) and alternating tangential flow systems (ATF™, Refine Technology, Pine Brook, N.J., See e.g. U.S. Pat. No. 6,544,424; Furey (2002) Gen. Eng. News. 22 (7), 62-63). The permeate may be drawn from the filters by use of peristaltic pumps. In a preferred embodiment perfusion is accomplished by use of an alternating tangential flow system.

Cell Culture Processes

Cell culture can be carried out under conditions for small to large scale production of recombinant proteins using culture vessels and/or culture apparatuses that are conventionally employed for animal or mammalian cell culture. As is appreciated by those having skill in the art, tissue culture dishes, T-flasks and spinner flasks are typically used on a laboratory bench scale. For culturing on a larger scale equipment such as, but not limited to, fermentor type tank culture devices, air lift type culture devices, fluidized bed bioreactors, hollow fiber bioreactors, roller bottle cultures, stirred tank bioreactor systems, packed bed type culture devices, and single use disposable bags or any other suitable devise known to one skilled in the art, can be used. Microcarriers may be used with the roller bottle or stirred tank bioreactor systems. The systems can be operated in a batch, fed-batch or perfusion/continuous mode. In addition, the culture apparatus or system may be equipped with additional apparatus, such a cell separators using filters, gravity, centrifugal force, and the like.

The production of recombinant proteins can be done in multiple phase culture processes. In a multiple phase process, cells are cultured in two or more distinct phases. For example cells may be cultured first in one or more growth phases, under environmental conditions that maximize cell proliferation and viability, then transitioned to a production phase, under conditions that maximize protein production. In a commercial process for production of recombinant proteins by mammalian cells, there are commonly multiple, for example, at least about 2, 3, 4, 5, 6, 7, 8, 9, 10 or more growth phases that occur in different culture vessels (N–x to N–1) preceding a final production culture. The growth and production phases may be preceded by, or separated by, one or more transition phases. A production phase can be conducted at large scale.

The term "growth phase" of a cell culture refers to the period of exponential cell growth (i.e., the log phase) where the cells are generally rapidly dividing. Cells are maintained at the growth phase for a period of about one day, or about two days, or about three days, or about four days, or longer than four days. The duration of time for which the cells are maintained at growth phase will vary based on the cell-type and/or the rate of cell growth and/or the culture conditions, for example.

The term "transition phase" refers to a period of time between the growth phase and the production phase. Generally, transition phase is the time during which culture conditions may be controlled to support a shift from growth phase to production phase. Various cell culture parameters which may be controlled include but are not limited to, one or more of, temperature, pH, osmolality, vitamins, amino acids, sugars, peptones, ammonium, salts and the like.

The term "production phase" of a cell culture refers to the period of time where the cell growth has plateaued. The logarithmic cell growth typically ends before or during this phase and protein production takes over. Fed batch and perfusion cell culture processes supplement the cell culture medium or provide fresh medium so as to achieve and maintain desired cell density, viability and product titer at this stage. A production phase can be conducted at large scale. Large scale cell cultures can be maintained in a volume of at least about 100, 500, 1000, 2000, 3000, 5000, 7000, 8000, 10,000, 15,000, 20,000 liters. In an embodiment of the invention, the production phase is conducted in 500 L, 1000 L and/or 2000 L bioreactors.

Typically the cell cultures that precede a final production culture go through two prior phases, seed and inoculum trains. The seed train phase (N-X) takes place at small scale where cells are quickly expanded in number. At the inoculums train phase (N–1), cells are further expanded to generate the inoculum for the production bioreactor, such as an inoculums of at least $0.5 \times 10^6$ cells/mL. Seed and N–1 trains can be produced by any culture method, typically batch cell cultures. N–1 cell densities of >$0.5 \times 10^5$ cells/mL are typical for seeding production bioreactors. Higher N–1 cell densities can decrease or even eliminate the time needed to reach a desired cell density in the production bioreactor. A preferred method for achieving higher N–1 cell densities is perfusion culture using alternating tangential flow filtration. An N–1 cell culture grown by means of a perfusion process using alternating tangential flow filtration can provide cells at any desired density, such as densities of >$90 \times 10^6$ cells/mL or more. The N–1 cell culture can be used to generate a single bolus inoculation cultures or can be used as a rolling seed stock culture that is maintained to inoculate multiple production bioreactors. The inoculation density can have a positive impact on the level of recombinant protein produced. Product levels tend to increase with increasing inoculation density. Improvement in titer is tied not only to higher inoculation density, but is likely to be influenced by the metabolic and cell cycle state of the cells that are placed into production. In one embodiment of the invention the cell culture is established by inoculating the bioreactor with at least $0.5 \times 10^6$ cells/mL.

The term "cell density" refers to the number of cells in a given volume of culture medium. "Viable cell density" refers to the number of live cells in a given volume of culture medium, as determined by standard viability assays (such as trypan blue dye exclusion method). The term "packed cell volume" (PCV), also referred to as "percent packed cell volume" (% PCV), is the ratio of the volume occupied by the cells, to the total volume of cell culture, expressed as a percentage (see Stettler, et al., (2006) Biotechnol Bioeng. December 20:95(6):1228-33). Packed cell volume is a function of cell density and cell diameter; increases in packed cell volume could arise from increases in either cell density or cell diameter or both. Packed cell volume is a measure of the solid level in the cell culture.

Cell Culture Controls

Cell culture conditions suitable for the methods of the present invention are those that are typically employed and known for batch, fed-batch, or perfusion (continuous) culturing of cells or any combination of those methods, with attention paid to pH, dissolved oxygen ($O_2$), and carbon dioxide ($CO_2$), agitation and humidity, and temperature. During recombinant protein production it is desirable to have a controlled system where cells are grown for a desired time or to a desired density and then the physiological state of the cells is switched to a growth-limited or arrested, high productivity state where the cells use energy and substrates to produce the recombinant protein in favor of increasing cell density. For commercial scale cell culture and the manufacture of biological therapeutics, the ability to limit or arrest cell growth and being able to maintain the cells in a growth-limited or arrested state during the production phase is very desirable. Such methods include, for example, temperature shifts, use of chemical inducers of protein production, nutrient limitation or starvation and cell cycle inhibitors, either alone or in combination.

One such mechanism for limiting or arresting growth is to shift the temperature during the cell culture. Temperature shifts may occur at any time during the cell culture. A growth phase may occur at a higher temperature than a production phase. A cell culture may be run at a first temperature set-point from about 35° C. to about 38° C., and then the temperature shifted to a second temperature set-point from about 29° C. to about 37° C., optionally from about 30° C. to about 36° C. or from about 30° C. to about 34° C. In one embodiment, a temperature shift may occur during the transition between the growth phase and the production phase. In another embodiment, a temperature shift may occur during the production phase.

Switching the temperature set-point may be done manually or can be done automatically by making use of bioreactor control systems. The temperature set-point may be switched at a predetermined time or in response to one or more cell culture parameters, such as cell density, titer, or concentration of one or more media components. One such method uses an online biomass monitoring tool integrated into the bioreactor control system to trigger a temperature set-point change when a desired cell density is reached. For example, a capacitance based biomass probe may be used for online cell density estimation and the data from online measurements can be used to trigger a shift in the bioreactor temperature. Such capacitance based probes include Fogale capacitance sensor (DN12-200) (Nimes, France).

Chemical inducers of protein production, such as caffeine, butyrate, and/or hexamethylene bisacetamide (HMBA), may be added independent of or at the same time as, before, or after a temperature shift. If inducers are added after a temperature shift, they can be added from one hour to five days after the temperature shift, optionally from one to two days after the temperature shift. The cell cultures can then be maintained for days or even weeks while the cells produce the desired protein(s).

Another method to maintain cells at a desired physiological state is to induce cell growth-arrest by exposure of the cell culture to low L-asparagine conditions (see e.g., WIPO Publication No. WO2013/006479). Cell growth-arrest may be achieved and maintained through a culture medium that contains a limiting concentration of L-asparagine and maintaining a low concentration of L-asparagine in the cell culture. Maintaining the concentration of L-asparagine at 5 mM or less can be used to maintain cells in a growth-arrested state.

Cell cycle inhibitors, compound known or suspected to regulate cell cycle progression and the associated processes of transcription, DNA repair, differentiation, senescence and apoptosis related to this are also useful to induce cell growth-arrest. Cell cycle inhibitors that interact with the cycle machinery, such as cyclin-dependent kinases (CDKs) are useful as are those molecules that interact with proteins from other pathways, such as AKT, mTOR, and other pathways that affect, directly or indirectly, the cell cycle.

Harvest and Purification

The expressed recombinant proteins may be secreted into the culture medium from which they can be recovered and/or collected. The recombinant proteins may then be subjected to one or more processing steps including harvest, purification, endotoxin and/or viral inactivation/filtration, and/or ultrafiltration/diafiltration.

The expressed recombinant proteins may be captured in the harvest permeate. The proteins may be purified, or partially purified, from harvest permeates using processes and commercially available products known in the art and/or available from commercial vendors. Such methods include flocculation; centrifugation; precipitation; filtration methods such as depth filtration; chromatography methods including, affinity chromatography, size exclusion chromatography, ion exchange chromatography, mixed mode anion exchange chromatography, hydrophobic interaction chromatography and hydroxyapatite chromatography, among other available methods.

The purified proteins can then be "formulated", meaning buffer exchanged, sterilized, bulk-packaged, and/or packaged for a final user. Suitable formulations for pharmaceutical compositions are known in the art and include those described in Remington's Pharmaceutical Sciences, 18th ed. 1995, Mack Publishing Company, Easton, Pa.

Process Analytical Techniques

Process analytical technologies and methods are available to monitor and evaluate samples taken during cell culture and purification processes to quantitatively and/or qualitatively monitor characteristics of the recombinant protein and the production process. This real time or inline information can be used to monitor and/or control product and production parameters, such as titer, cell density; product quality attributes such as post translational modifications; product or process variability such as impurities and the like, to make timely decisions and modify processes as necessary.

Each step of an upstream cell culture process or a downstream purification process may be monitored to provide information about the amount of a particular product quality attribute (PQA) and to control this PQA with a preset target and range.

Samples may be taken intermittently, at desired frequencies, or continuously. Samples may be analyzed in real time or near real time or stored for later analysis. This information can be used to make changes during upstream and downstream processes.

Detection of product quality attribute may be done using mass spectrometry, liquid chromatography with UV and/or mass spectrometry detection and capillary electrophoresis and the like.

These processes are adaptable to continuous monitoring with manual or automated process adjustments such as feeds, temperature, process duration as determined by the level of a specified product quality attribute.

Intact mass analysis to detect the presence of post-translational modifications such as amino acid processing and glycosylation may be made using a polyhydroxyethyl aspartamide column operated in size-exclusion mode and coupled with ESI-MS (Brady et al., (2008) J Am Soc Mass Spectro, 19: 502-509)

Real-time monitoring eluate from ion exchange chromatography by monitoring a normalized LS/UV ratio for each fraction using laser light scattering detector and an UV absorbance, see US Patent Publication No. US 2013-0303732.

Multi-attribute method makes use of single liquid-chromatography/mass spectrometry (LC/MS) to search and characterize tandem MS data using various database and search platforms such as Sequest (The Scripps Research Institute, La Jolla, Calif.), X! Tandem (The Global Proteome Machine Organization) or Mascot (Matrix Science, Boston, Mass.). Samples may be denatured at high pH or to maintain disulfide isoforms and protect succinimide variants, at low pH. The sample is then reduced and alkylated followed by digestion with trypsin. The sample is then injected into an MS (such as a Q Exactive™ Hybrid Quadrupole-Orbitrap Mass Spectrometer, Thermo Fischer Scientific, Waltham, Mass.) and analysis is performed using Pinpoint software (Thermo Fischer Scientific). Attributes that can be identified, quantified and monitored include isomerization, deamination, disulfide reduction, host cell protein contamination, mutations, misincorporations, hydroxylysine, thioether, non-glycolysated heavy chains, C-terminal amidation, residual protein A, characterize glycans and provide molecule identity. The mass accuracy for each attribute monitored can be set at less than 5 ppm of the predicted mass. Identification of the peptide/attribute is confirmed by MS2 fragmentation and orthogonal characterization methods (HILIC-MS for glycosylation for example). The experimental isotopic distribution must have a dot product score better than 0.95 when compared to the theoretical isotopic distribution. A retention time window is set for each attribute and all detectable charge states for each attribute are considered for quantification. A criteria is defined that will detect changes in the attribute. For example, deamination can be monitored by determining a deamination value (deaminated peptide divided by the sum of the deaminated peptide and the unmodified parent peptide multiplied by 100. Glycosylation can be monitored by comparing each specific glycan to the sum of all detectable glycans.

Proteins

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation resulting in glycoproteins, lipid attachment, sulfation, gamma-carboxylation of glutamic acid residues, hydroxylation and ADP-ribosylation.

As used herein, the term "glycoprotein" refers to peptides and proteins having at least one oligosaccharide side chain including mannose residues. Glycoproteins may be homologous to the host cell, or may be heterologous, i.e., foreign, to the host cell being utilized, such as, for example, a human glycoprotein produced by a Chinese hamster ovary (CHO) host cell. Such glycoproteins are generally referred to as "recombinant glycoproteins." In certain embodiments, glycoproteins expressed by a host cell are directly secreted into the medium.

Proteins can be of scientific or commercial interest, including protein-based drugs. Proteins include, among other things, antibodies and fusion proteins. Peptides, polypeptides and proteins may be produced by recombinant animal cell lines using cell culture methods and may be referred to as "recombinant peptide", "recombinant polypeptide", "recombinant protein", "recombinant glycoprotein". The expressed protein(s) may be produced intracellularly or secreted into the culture medium from which it can be recovered and/or collected.

Nonlimiting examples of mammalian proteins that can be advantageously produced by the methods of this invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682; Riegg and Pytela (1995), Gene 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-β, leukemia inhibitory factor, and oncostatin-M. Descriptions of proteins that can be produced according to the inventive methods may be found in, for example, *Human Cytokines: Handbook for Basic and Clinical Research, all volumes* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook, Vols. 1 and 2* (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI (Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD19, CD20, CD22, CD23, CD25, CD27 L, CD32, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-12, IL-12 p35 subunit, IL-13, IL-21, IL-23, IL-23 p19 subunit, IL-12/IL-23 shared p40 subunit, IL-2 receptor, IL-4 receptor, IL-6 receptor, IL-13 receptor, IL-17 receptor, IL-18 receptor subunits, FGL2, PDGF-β and analogs thereof (see U.S. Pat. Nos. 5,272,064 and 5,149,792), B7RP-1, B7RP-2, VEGF, TGF, TGF-β2, TGF-β1, c-fms, EGF receptor (see U.S. Pat. No. 6,235,883), CGRP receptor, VEGF receptor, hepatocyte growth factor, proprotein convertase subtilisin/kexin type 9 (PCSK9), FGF21, osteoprotegerin ligand, interferon gamma, EGFRvIII, B lymphocyte stimulator (BlyS, also known as BAFF, THANK, TALL-1, and zTNF4; see Do and Chen-Kiang (2002), *Cytokine Growth Factor Rev.* 13(1): 19-25), ST2, C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TSLP, IFNγ, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), angiopoietin 1 (Ang1), angiopoietin 2 (Ang2), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), programmed cell death 1 (PD-1), programmed cell death ligand 1 (PDL-1), programmed cell death ligand 2 (PDL-2), lymphocyte activation gene-3 (LAG-3), T-cell immunoglobulin domain and mucin domain 3 (TIM3), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, alirocumab, bevacizumab, infliximab, abciximab, alemtuzumab, bapineuzumab, basiliximab, belimumab, briakinumab, brodalumab, canakinumab, certolizumab pegol, cetuximab, conatumumab, denosumab, dupililumab, eculizumab, gemtuzumab guselkumab, ozogamicin, golimumab, ibritumomab, ixekizumab, ipilimumab, tiuxetan, labetuzumab, lebrikizumab, mapatumumab, mavrilimumab, matuzumab, mepolizumab, motavizumab, muromonab-CD3, nivolumab, natalizumab, nimotuzumab, ofatumumab, omalizumab, oregovomab, palivizumab, panitumumab, pemtumomab, pertuzumab, pembrolizumab, ranibizumab, rituximab, romosozumab, rovelizumab, rilotumumab, tildrakizumab, tocilizumab, tositumomab, tralokinumab, trastuzumab, tremelimumab, ustekinumab, vedolizomab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05; Harbury et al. (1994), *Nature* 371:80-83; Hakansson et al. (1999), Structure 7:255-64. Specifically included among such recombinant fusion proteins are proteins in which a portion of a receptor is fused to an Fc portion of an antibody such as etanercept (a p75 TNFR:Fc), and belatacept (CTLA4:Fc). Chimeric proteins and polypeptides, as well as fragments or portions, or mutants, variants, or analogs of any of the aforementioned proteins and polypeptides are also included among the suitable proteins, polypeptides and peptides that can be produced by the methods of the present invention. This includes trebananib, an angiopoietin (Ang) 1 and 2 neutralizing peptibody. Also included are bi-specific T-cell engagers (BiTEs) that exert action selectively and direct the human immune system to act against tumor cells. Specifically included among such BiTEs are that target CD19, such as blinatumomab. Other molecules include aflibercept.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990). All documents, or portions of documents, cited in this application, including but not limited to patents, patent applications, articles, books, and treatises, are hereby expressly incorporated by reference. What is described in an embodiment of the invention can be combined with other embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Cell Culture

On day 0, CHO cells expressing a recombinant anti-TNFα antibody were inoculated into 3 L bioreactors (Applikon, Foster City, Calif.) at $9.0 \times 10^6$ viable cells/mL in a working volume of 1500 ml of a serum-free, chemically-defined base medium. The cultures were maintained at 36° C., DO at 30 mmHg, agitation at 400 RPM. The cell cultures were initiated in batch mode and perfusion was started on day 3 using an ATF-2™ alternating tangential flow filtration system (Refine Technologies, Hanover, N.J.) equipped a 30 kDa NFWC GE RTP Hollow Fiber Cartridge (GE Healthcare, Pittsburgh, Pa.). The medium was a serum-free, chemically-defined perfusion medium including manganese sulfate monohydrate and cupric sulfate pentahydrate and pH as described in Table 1. The experiment was run in duplicate.

TABLE 1

| pH | $Mn^{2+}$ (nM) | $Cu^{2+}$ (ppb) |
|---|---|---|
| 6.85 | 50 | 10 |
| 6.85 | 50 | 100 |
| 6.85 | 1000 | 10 |
| 6.85 | 1000 | 100 |
| 7.0 | 50 | 10 |
| 7.0 | 50 | 100 |
| 7.0 | 1000 | 10 |
| 7.0 | 1000 | 100 |

The perfusion rate increased gradually from 0.3 to 1.0 working volume/day over the cell culture run. On day, the temperature was shifted to 31° C. and the culture was harvested on day 17. Glucose was maintained between 4-8 g/L.

Samples were taken daily to assess the culture. The pH and partial pressure of $CO_2$ ($pCO_2$) and $O_2$ ($pO_2$) were measured using a Rapid Lab 1260 blood gas analyzer (Siemens, Malvern, Pa.); concentration of glucose and lactate, were measured using a NovaFLEX (Nova Biomedical, Waltham, Mass.). Osmolality by determined by Model 2020 Osmometer (Advanced Instruments, Norwood, Mass.). Temperature, pH, dissolved oxygen and agitation were controlled using Applikon ADI1010 controllers.

On days 7, 10, 13, 15 and 17, 50 mL samples of the culture were removed from the bioreactors for product quality analysis. The samples were centrifuged at 3000 rpm for 30 minutes at room temperature (Beckman Coulter, Indianapolis, Ind.) and the supernatant was filtered through a 0.2 µm tube top filter (Corning, Fisher Scientific, Pittsburgh, Pa.). Cell free supernatant was then frozen at −20° C. until thawed and Protein A purified prior to product quality analysis. Upon completion of the 17 day production, the remaining culture was removed from the bioreactors. Cells were separated from the supernatant by centrifugation at 3000 rpm for 30 minutes at 4° C. and the conditioned culture medium was sterile filtered using a 0.2 µm polyethersulfone (PES) cartridge filter into Nalgene bottles (Fisher Scientific, Pittsburgh, Pa.), then purified by Protein and the neutralized eluates were tested as described above.

Viable cell density and cell viability were deterred by Vi-Cell (Beckman Coulter, Brea, Calif.). Integrated viable cell density (IVCD) was calculated as a cumulative viable cell density over the entire length of the production. Titer was measured using POROS® Protein A (Life Technologies, Grand Island, N.Y.). Titer was determined in the supernatant and then adjusted for the volume that was occupied by the cells so that it was representative of what was actually present in a given volume of cell culture fluid. Since packed cell volume was expressed as a percent of the total volume, the PCV adjusted titers was always lower than the titer in the supernatant.

Different N-glycan species were analyzed by hydrophilic-interaction liquid chromatography (HILIC) and are presented as a percent of the total peak area of the combined glycans. Antibody-containing samples were collected and purified by Protein A. The purified samples were treated with PNGase-F and incubated at 37° C. for 2 hours to release the N-linked glycans. The enzymatically released glycans were labeled with 2-aminobenzoic acid (2-AA) at 80° C. for 75 minutes. Excess 2-AA label was then removed with a Glycoclean S cartridge. The samples were evaporated overnight and the resulting dry pellet was reconstituted with water for subsequent HILIC analysis, using UPLC (Waters Corporation, Milford, Mass.). The glycans were injected and bound to the column in high organic conditions and eluted with an increasing gradient of an aqueous ammonium formate buffer. Fluorescence detection was used to monitor the glycan elution and the relative percentage of the major and minor glycan species were calculated. β-gal levels include A1G1F, A2G1F, A2G2F and the analogous afucosylated forms. Afucosylated forms include A1G0, A2G0, A1G1, A2G1 and A2G2. Mannose 5 and Mannose 7 were also determined.

This experiment was designed to define the effects of each main factor (copper, manganese, and pH) and two way interactions. The experiment was a three factor, two level ($2^3$) full factorial design to define main effects and two way interactions and did not include center points. The study was intended to deliver power values of approximately 0.8 using a signal to noise ratio of 1.25. Profiles were generated using JMP statistical software and Prediction Profiler (SAS Institute, Inc., Cary, N.C.).

Results

The concentration of copper and manganese in the perfusion medium did not impact cell culture performance or productivity. While pH did not impact cell growth or productivity, pH 6.85 reduced final viability by approximately 10% ($p<0.001$), FIGS. 1-4.

High Mannose Glycans pH was the only factor that had a significant effect on high mannose levels. As pH increased, so did the level of high mannose, see Table 2.

β-galactosylation

The addition of manganese enhanced the β-galactosylation. The greater the concentration of manganese, the greater the percentage of β-galactosylation. pH had a statistically significant effect to β-galactosylation as well. Increasing pH increased 3-galactosylation but to a lesser extent than when compared to the increase when manganese was added, see FIG. 5. The effect of copper on β-galactosylation was insignificant.

Afucosylation

Copper, manganese and pH all had a statistically significant impact on the afucosylation levels. The greater the concentration of copper and manganese and the higher the pH, the higher the level of afucosylation, see FIG. 6.

All of the key glycans were significantly impacted by pH. β-galactosylation was significantly impacted by increasing manganese concentration. Increasing the level of manganese to its highest level resulted in an increase of j3-galactosylation by approximately 14% over the base line, lowest level of copper and manganese tested at the same pH, as determined by statistical modeling. Afucosylation was significantly impacted by increasing both copper and manganese concentrations. Increasing the levels of copper and manganese enhanced the level of afucosylation by approximately 1.3% over the base line value. While the addition of high concentrations of copper and manganese had no impact on cell culture performance, they did have an impact on product quality. See Tables 2 and 3.

TABLE 2

Results from day 17 harvest

| $Mn^{+2}$ (nM) | $Cu^{+2}$ (ppb) | pH | Afucosylation (%) | High Mannose (%) | β-galactosylation (%) |
|---|---|---|---|---|---|
| 50 | 10 | 6.85 | 4.24 | 2.69 | 16.14 |
| 50 | 10 | 7.00 | 5.19 | 3.55 | 18.71 |
| 50 | 100 | 6.85 | 4.83 | 2.54 | 16.09 |

TABLE 2-continued

Results from day 17 harvest

| $Mn^{+2}$ (nM) | $Cu^{+2}$ (ppb) | pH | Afucosylation (%) | High Mannose (%) | β-galactosylation (%) |
|---|---|---|---|---|---|
| 50 | 100 | 7.00 | 5.93 | 3.32 | 21.90 |
| 1000 | 10 | 6.85 | 4.94 | 2.63 | 30.79 |
| 1000 | 10 | 7.00 | 6.26 | 3.21 | 35.14 |
| 1000 | 100 | 6.85 | 5.46 | 2.53 | 29.31 |
| 1000 | 100 | 7.00 | 6.59 | 3.36 | 32.93 |

TABLE 3

Summary of the model fit ($R^2$) and the statistical significance of the terms that are part of the model (p values).

| Parameter | Adjusted $R^2$ | Higher pH P Values | Higher $Mn^{2+}$ P Values | Higher $Cu^{2+}$ P Values |
|---|---|---|---|---|
| β-Galactosylation | 0.95 | 0.0028 | <0.0001 | — |
| Afucosylation | 0.92 | <0.0001 | <0.0001 | 0.0028 |
| High Mannose | 0.93 | <0.0001 | — | — |

Glycosylation can affect therapeutic efficacy of recombinant protein drugs. It is well known that variations in Fc glycosylation can affect Fc-mediated effector functions. Afucosylation and high mannose glycans can enhance antibody-dependent cellular cytotoxicity (ADCC) activity. For use in a ADCC assay, afucosylated and fucosylated recombinant anti-TNFα antibody material was produced separately using a fed-batch process. Afucosylated antibody was made with the aid of an added fucosyltransferase inhibitor. The resultant recombinant antibody was about 85% afucosylated. The afucosylated antibody material was then mixed with completely fucosylated antibody material to produce specific levels of afucosylation in the final antibody mixture. The antibody material was then used to measure the level of ADCC activity at various levels of afucosylation to determine the sensitivity of the ADCC response.

The ADCC activity of the antibody mixture was evaluated in a cell-based assay using CHO M7 cells that stably expressed a TNFα converting enzyme (TACE)-resistant form of transmembrane TNFα as target cells. NK92-M1 cells, stably transfected with human CD16 (FcγRIIIa-158V) were used as effector cells. Briefly, target cells were opsonized with increasing concentrations (0.143 ng/mL to 40 ng/mL) of antibody prior to co-incubation with the NK92-M1/CD16 effector cells. Upon ADCC-mediated target cell lysis, the intracellular enzyme adenylate kinase was released into the cell culture medium. The amount of adenylate kinase released was measured using the ToxiLight™ Bioassay Kit (Lonza, Allendale, N.J.). SoftMax® Pro (Molecular Devices, Sunnyvale, Calif.) was used to perform a 4-parameter data analysis and a constrained model curve fit to the dose-response data. Test sample activity was determined by comparing the test sample response to the response obtained for the reference standard and was reported as percent relative cytotoxicity.

For use in a complement-dependent cytotoxicity (CDC) assay, β-galactosylated material that was obtained from a chromatographically enriched fraction of the recombinant anti-TNFα antibody. The enriched antibody was used to prepare solutions with specific levels of β-galactosylation. The level of CDC activity at various levels of β-galactosylation was then measured to establish the sensitivity of the CDC response.

The degree of CDC activity elicited by the antibody was evaluated in a functional cell based assay. CHO M7 cells were pre-incubated with 20 μM calcein-AM (Sigma, St. Louis, Mo.). The calcein-AM entered the cells and was cleaved by nonspecific esterases to become fluorescent and trapped within the intact cell membranes. The calcein-loaded target cells were incubated with different dose concentrations of the antibody (1.563 ng/mL to 200 ng/mL), followed by complement addition (2.5% final concentration) for a second incubation.

After the complement incubation, the supernatant was removed and the fluorescence was measured using a microplate reader (EnVision, Perkin Elmer, Waltham, Mass.). The fluorescence intensity was directly proportional to the amount of cellular lysis. SoftMax® Pro (Molecular Devices, Sunnyvale, Calif.) was used to perform a 4-parameter data analysis and a constrained model curve fit to the dose response data. Test sample activity was determined by comparing the test sample response to the response obtained for the reference standard and was reported as percent relative cytotoxicity.

Increasing the level of afucosylation by as little as 2% had a practical impact on ADCC activity (FIG. 7). CDC activity was also clearly impacted by increasing the level of β-galactosylation, although the response was much less sensitive (FIG. 8).

ADCC and CDC effector functions can be critical factors for the clinical activity of therapeutic proteins and achieving desired target values for specific glycans may be key to reaching desired clinical endpoints. Small changes in afucosylation can have a big impact on the ADCC activity of a glycoprotein. By altering copper and manganese it is possible to control the levels of glycans that are responsible for these effector functions and direct the product quality.

What is claimed is:

1. A method for manipulating the fucosylated glycan content on a recombinant protein comprising
   inoculating a bioreactor with mammalian host cells expressing the recombinant protein,
   culturing the host cells in a serum free, chemically defined cell culture medium; wherein the cell culture medium includes from 10 to 100 ppb copper and from 50 to 1000 nM manganese,
   harvesting the recombinant protein produced by the host cell.

2. The method of claim 1, wherein there is also an increase in the level of β-galactosylation on the recombinant protein.

3. The method according to claim 1, wherein the concentration of copper is 100 ppb.

4. The method according to claim 1, wherein the concentration of manganese is 1000 nM.

5. The method according to claim 1, wherein the fucosylated glycan content is manipulated to influence the level of afucosylated and β-galactosylated glycans without impacting cell culture performance.

6. The method according to claim 1, further comprising a temperature shift.

7. The method according to claim 6, wherein the temperature shift is from 36° C. to 31° C.

8. The method according to claim 6, wherein the temperature shift occurs at the transition between the growth phase and production phase.

9. The method according to claim 6, wherein the temperature shift occurs during the production phase.

10. The method according claim 1 wherein the host cell expressing the recombinant protein is cultured in a batch culture, fed-batch culture, perfusion culture, or combinations thereof.

11. The method according to claim 10, wherein the culture is a perfusion culture.

12. The method according to claim 11, wherein perfusion comprises continuous perfusion.

13. The method according to claim 11, wherein the rate of perfusion is constant.

14. The method according to claim 11, wherein the perfusion is performed at a rate of less than or equal to 1.0 working volumes per day.

15. The method according to claim 11, wherein the perfusion is accomplished by alternating tangential flow.

16. The method according to claim 1, wherein the bioreactor has a capacity of at least 500 L.

17. The method according to claim 1 wherein the bioreactor has a capacity of at least 500 L to 2000 L.

18. The method according to claim 1 wherein the bioreactor has a capacity of at least 1000 L to 2000 L.

19. The method according to claim 1, wherein the bioreactor is inoculated with at least $0.5 \times 10^6$ cells/mL.

20. The method according to claim 1, wherein the serum-free chemically defined cell culture medium is a perfusion cell culture medium.

21. The method according to claim 1, wherein the host cells are Chinese Hamster Ovary (CHO) cells.

22. The method according to claim 1, wherein the recombinant protein is a glycoprotein.

23. The method according to claim 1, wherein the recombinant protein is selected from the group consisting of a human antibody, a humanized antibody, a chimeric antibody, a recombinant fusion protein, or a cytokine.

24. The method according to claim 1, wherein the recombinant protein produced by the host cell is purified and formulated into a pharmaceutically acceptable formulation.

* * * * *